United States Patent [19]

Padula, II et al.

[11] 4,252,419
[45] Feb. 24, 1981

[54] OPHTHALMIC MEASURING INSTRUMENT

[76] Inventors: William V. Padula, II, 32 Wauwinet Ct., Guilford, Conn. 06437; William V. Padula, I, 299 Manor Ave., Cranford, N.J. 07016

[21] Appl. No.: 70,981

[22] Filed: Aug. 30, 1979

Related U.S. Application Data

[63] Continuation-in-part of Ser. No. 809,536, Jun. 24, 1977, Pat. No. 4,190,331.

[51] Int. Cl.³ .............................................. A61B 3/10
[52] U.S. Cl. .......................................... 351/5; 33/200
[58] Field of Search ................... 351/5, 9, 26; 33/200; 356/127

[56] References Cited

PUBLICATIONS

Engelmann, Subjective Pupillary Distance Measurement, The Optometric Weekly, 9/28/61.

*Primary Examiner*—John K. Corbin
*Assistant Examiner*—Rodney B. Bovernick
*Attorney, Agent, or Firm*—Daniel H. Bobis

[57] ABSTRACT

An ophthalmic measuring instrument has an instrument frame with suitable clips for mounting the instrument frame to an eyeglass frame on the patient so that spaced eye viewing openings on the instrument frame of the ophthalmic measuring instrument are disposed in alignment with the position of the lenses for the given eyeglass frame to which the instrument frame is attached. Transparent yellow and blue strips having respectively sized widths are adjustably mounted on the instrument frame for movement relative the eye viewing openings and for intersecting movement relative each other. The patient can, in an adjusted position of said yellow and blue strips, view white square targets of predetermined size as a function of the specific working or reading distance at which said targets are being viewed. By centering the instrument frame on the eyeglass frame, and monocularly occluding the patient's respective left eye and right eye, movement of first the yellow strip and then the blue strip, bisecting the patient's visual axes respectively for the left eye and the right eye will enable various measurements to be obtained, such as the exact inter-visual axes distance relative to the center of the eyeglass frames for near vision. The horizontally disposed blue strip can be provided with suitable bracket means for receiving a corrective lens where a patient has a refractive error or presbyopia.

3 Claims, 5 Drawing Figures

OPHTHALMIC MEASURING INSTRUMENT

This application is a continuation-in-part of co-pending application Ser. No. 809,536 now U.S. Pat. No. 4,190,331 filed June 24, 1977.

BACKGROUND OF THE INVENTION

This invention relates generally to devices for measuring eyes and more particularly to an ophthalmic measuring instrument which can be applied directly to an eyeglass frame selected by the patient so that a monocular measurement of the patient's visual axis can be obtained for each respective eye, which measurements are critical in prescribing lenses, telescopes, and microscopes for patients with special optical needs.

Certain words of art are utilized in the present application and when used herein, these words are defined as follows:

a. Geometric axis of the eye is the imaginary line passing through the anterior and posterior poles of the given eyeball.

b. Pupillary axis is the imaginary line perpendicular to the corner and passing through the center of the entrance pupil of the eye.

c. Visual axis is the imaginary line connecting the fovea (the point on the retina which fixates on a target) to the point of fixation on the target and passing through the nodal points of the eye.

d. PD is the shortened term for pupillary distance which is the distance between the respective pupillary axis of each eye.

For the normal eye, the pupillary axis closely parallels the geometric axis. The PD or pupillary distance is a topographical measurement that is used to grossly determine the direction in which the eyes are gazing.

The visual axis however is a psychophysical imaginary line which precisely connects the fovea and the target being viewed.

When formulating the prescription for corrective lenses, the conventional technique for determining the geometric centers for such corrective lenses is to measure the pupillary distance (PD) for the patient's eyes. This has been done by the examiner's use of a metric ruler or other device for measuring objectively the distance between the inner edge of one pupil and the outer edge of the other pupil of the patient's eyes as the eyes are fixed on a far point target and then on a near point target.

Because of the importance of these measurements to the examiner in determining the proper prescription for the patient's lenses particularly in low vision patients, various devices are known in the prior art for making accurate objective measurements of the PD distance for a patient's eyes such as is shown in U.S. Pat. Nos. 1,052,161, and 2,197,139, and 2,491,312 and at least U.S. Pat. No. 2,884,832 outlines a method for patient or subjective measurement of PD.

In U.S. Pat. No. 2,491,312 the problems and the reasons for such measurements particularly in the filling and providing of bi-focal and multi-focal lenses are set forth in some detail.

It has been found that scrupulously derived results from the conventional twenty-one point optometric examination can be voided by inaccurate PD measurements for the far point and near point working distances of the patient.

Some prior art methods of measurement may be adequate to provide PD measurements for distance vision excepting eccentric fixation. However, the use thereof for providing the PD measurement for near vision often results in errors which can cause induced prism and cylinder, in turn causing asthenopic and even aniseikonic symptoms. Prentice's rule known to those skilled in the art has shown that prism is a function of dioptric power times centemeters of displacement. Therefore, any error in these conventional methods of objective measurement of PD become critical when prescribing a high dioptric value prescription.

While in the normal eye, the pupillary axis closely parallels the geometric axis, one critical source of error which the conventional methods of objective measurement of PD distance for a patient's eyes does not and cannot account for is the known fact that the visual axis for the eye passes 1 mm. nasal to the geometric axis for the given eye. This nasal characteristic of the visual axis is not significant for distance vision because the visual axes are essentially parallel and therefore the conventional methods of objective measurement for the PD of the patient's eyes and the subjective or patient's measurements of the visual axes for the eyes will be essentially in agreement except for eccentric fixation.

When, however, these methods of measurements are applied to near vision, the inter-visual axes distance will be consistently smaller because of the convergence of the visual axes at the vertex distance of the plane of the eyeglass frame.

Such inaccuracies of the conventional objective measurement techniques can be tolerated for most spherocylindrical refractive errors. This is not the case for spherical refractive errors above 4.00 diopters (D) and cylinder above 1.00D and/or where a patient requires high refractive lenses, telescopes and/or microscopes. If these inaccuracies and errors are present they can cause many vision problems.

The monocular measurement of the patient's visual axis cannot be overlooked for the further reason that optical and facial assymetries can cause the geometric center of the lens for each eye to be displaced from the point at which the visual axes actually passes through the lens. Facial assymetry on each patient is such that the distance between each eye and the bridge of the nose is seldom equal.

In U.S. Pat. No. 2,884,832, a device and method is disclosed for measuring the inter-pupillary axes distance for a given patient's eyes by measuring the monocular pupillary axis distance for each of the respective eyes of the patient and the near convergence of the pupillary axes by measuring the pupillary distance (PD) for the combined or binocular action of both eyes. However, the device utilized with this method of measuring can introduce error when used for locating the position of the geometric or optical center in a lens prescription because the pupillary axis for a given eye does not intersect the plane of the lens at the same location as the visual axis.

The subjective use of a relatively wide filter strip in front of the patient's eye as described in the method of U.S. Pat. No. 2,884,832 and in the related article in the Optemetric Weekley 52:39 of Sept. 28, 1961 by the inventor, O.R. Engleman entitled—Subjective Pupillary Distance Measurement—permits the patient to project off-foveal or peripheral retina points to the pupillary margins and through the filter strips. This results in an extension of the pupillary angle of which the line will theoretically converge behind the eye. The line bisecting this angle is the pupillary axis.

Since the average pupil size is approximately 4 mm., using filter strips relatively larger than the pupil allows the pupillary angle and pupillary axis to be accurately measured by this method. However, this measurement can be grossly in error for prescription purposes because of the problem set forth above.

Further error is introduced by the method and device shown and described in U.S. Pat. No. 2,884,832 and the above-mentioned related article because it is difficult for the patient and the examiner to set and to maintain with the setting element thereof the vertical position of the visual axis for a given eye being measured, it does not allow vertical or horizontal measurement of the inclination of the visual axis which is important when prescribing spectacle-mounted telescopes and surgical binoculars, and the width of the target card used does not equal the visual angle subtended through the setting or viewing means of the device at the working distances.

The present invention seeks to meet and overcome these problems by providing a new device which permits the examiner to define the visual axis for each of the patient's eyes. This device is affixed to the eyeglass frame selected by the patient so that the center of the eyeglass frame serves as a reference point. On this device, adjustable relative narrow filter strips having a width in a range from 2 to 3 1½ mm. are mounted in front of each eye viewing window on the eyeglass frame for movement relative the associated eye viewing window and for intersecting relation to each other. By placing the eyeglass frame with the improved device in accordance with the present invention thereon, in position to the patient's face, and having the patient view sized targets for the near working distance therethrough, the patient can subjectively provide the examiner with measurements of; the monocular visual axis (MVA) distance of the respective eyes of the patient relative the center of the eyeglass frame; measurements of the exact horizontal and vertical displacement of the visual axes for the respective eyes of the patient, so as to eliminate all possible sources of error and provide a relatively simple standardized method for measuring the inter-visual axes for a patient's eyes from which an examiner can more accurately prescribe the required corrective lenses, telescopes and microscopes for patients with special optical needs.

Control of the width of the filter strips in the device according to the present invention so that the respective filter strips are narrower than the pupil of the given eye being examined is necessary for accurate measurement of the visual axis. When a filter strip narrower than the pupils is used, the fovea, the point on the retina of the eye is used to sight directly through the filter. The angle projected from the fovea through the filter is the visual angle. The imaginary line bisecting this angle is the visual axis.

Since, even in a normal eye, the visual axes passes through the cornea and the lens of the patient's eyeglasses nasal to the pupillary axis, the difference between the visual axis and the pupillary axis will become more pronounced when the pupil is displaced, defined as corectopea, by either pathology or surgery. Errors on these situations can produce differences between the pupillary axis and the visual axes at the plane of the lens of the eyeglass frame of as much as 6 to 7 mm. and if the conventional measurement of the pupillary axes is utilized, gross errors can be introduced in determining the prescription for the patient's lenses.

Thus, unlike prior art devices and methods such as is shown in U.S. Pat. No. 2,884,832 which measures only PD, the device in accordance with the present invention is measuring a completely different axes, namely the visual axes and provides a method for measuring the inter-visual axis so that the patient's prescription can be determined free of all possible sources of errors and with a precise position for the visual axes at the plane of the respective lenses in the patient's eyeglasses.

SUMMARY OF THE INVENTION

Thus, the present invention covers an ophthalmic measuring instrument having an instrument frame with means for mounting the same on the eyeglass frame of the patient, said instrument frame having spaced eye viewing openings therein and adjustably mounted intersecting transparent colored strips respectively sized in a predetermined width and movable for determining the visual axis for each of the patient's eyes with respect to a fixed and sized target, the instrument frame having index means thereon to provide substantially exact measurements for said monocular visual axis distance and the difference in the vertical positions of the visual axis for each respective eye of the patient.

Accordingly, it is an object of the present invention to provide an improved ophthalmic measuring instrument to provide subjective measurements of the near point and far point monocular visual axis.

It is another object of the present invention to provide an ophthalmic measuring instrument for measuring the inter-visual axes for a patient's eyes.

It is still another object of the present invention to establish a simple standardized procedure to eliminate errors in prescribing and designing lenses for various optical devices.

Other objects and advantages of the invention will be more fully brought out in the following description and accompanying drawings wherein.

Figure 1:
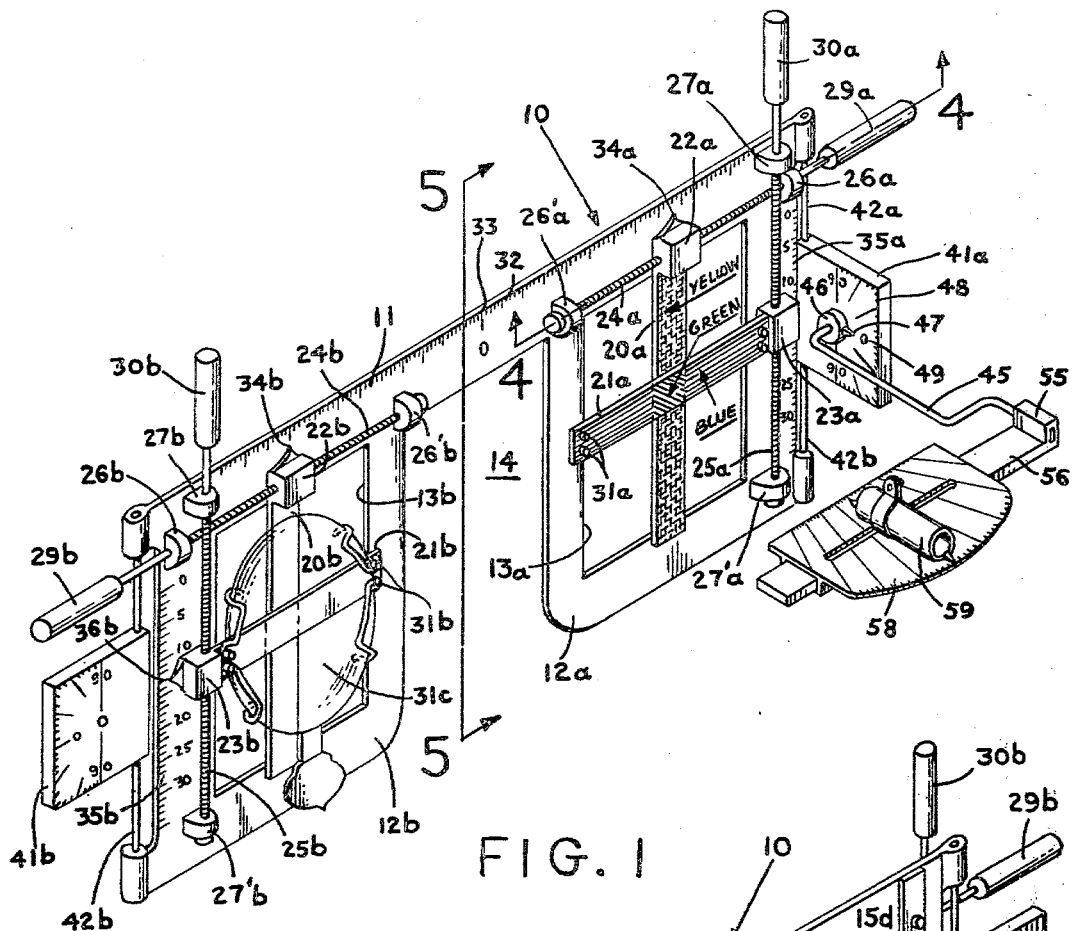
FIG. 1 is an isometric view of an ophthalmic measuring instrument in accordance with the present invention.
Figure 2:
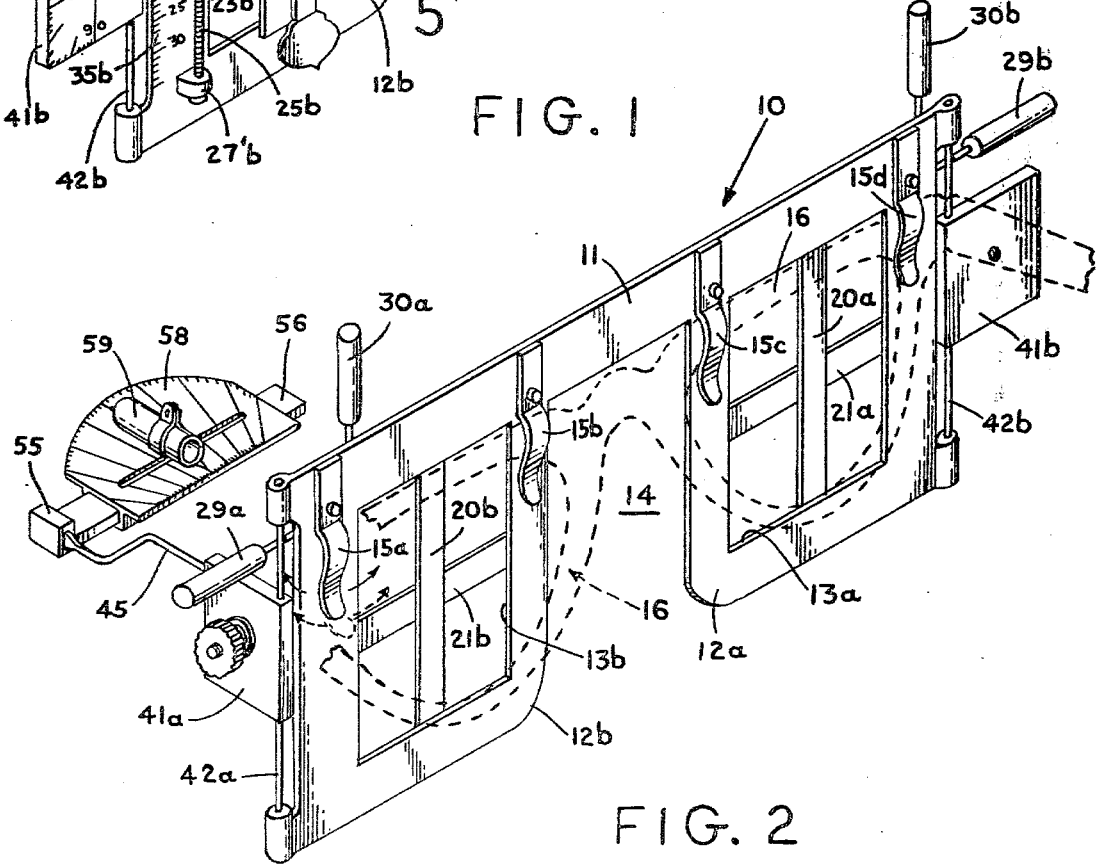
FIG. 2 is a rear isometric view of the ophthalmic measuring instrument shown in FIG. 1 illustrating the manner of applying the instrument to a selected eyeglass frame.

Referring to the drawings FIGS. 1 and 2 show a preferred form of ophthalmic measuring instrument in accordance with the present invention which has a main instrument frame generally designated 10 made of any suitable material such as aluminum, stainless steel or plastic.

The instrument frame 10 is a relatively thin flat elongated generally rectangular member having an elongated transverse member 11 and spaced side sections 12a and 12b which depend from and are in the same plane as the transverse member 11. The spaced side sections 12a and 12b are approximately the same thickness as the transverse member 11 and include spaced eye viewing openings as at 13a and 13b respectively therein and define a space as at 14 therebetween. Frame 10 is provided with clips 15a, 15b, 15c and 15d on the back thereof to permit the instrument frame to be mounted to an eyeglass frame generally designated 16 shown in phantomized form by the dotted lines in FIG. 2 so that the eye viewing openings 13a and 13b are disposed in alignment with the corresponding lens areas 17a and 17b on the eyeglass frame 16.

The ophthalmic measuring instrument has two types of measuring devices mounted on the instrument frame 10. The first is for measuring the monocular visual axis distance for each of the patient's eyes generally referred to herein as the MVA, and the second is for measuring the inclination and convergence of the visual axis for each of the respective eyes as will not be described.

MVA MEASURING ASSEMBLY

To accurately measure the MVA distance of the patient's eyes in accordance with the present invention, two intersecting transparent strips or elongated members are adjustably mounted as at 20a and 21a on the side section 12a and 20b and 21b on the side section 12b. The colored strips are not wider than 3½ millimeter and preferably will have a width in a range from 2 to 3½ mm. This width is necessary to an accurate measurement of the MVA for a given eye of the patient. Colored strips 20a and 20b are disposed vertically and in front of the eye viewing openings 13a and 13b and can be indexed to move right and left in the vertical plane in which they lie relative to the eye viewing openings 13a and 13b. Colored strips 21a and 21b also are disposed in front of eye viewing windows 13a and 13b, and horizontally oriented in an overlapping and intersecting relation with the colored strips 20a and 20b respectively. The colored strips 21a and 21b can be indexed to move up and down in the vertical plane in which they lie relative to the eye viewing openings 13a and 13b and to the colored strips 20a and 20b, as is shown in FIGS. 1 and 2 of the drawings.

The respective strips 20a and 20b are preferably colored yellow and the strips 21a and 21b will be colored blue. This difference in color for the respective vertical and horizontal strips is selected because they are complimentary colors and as is more fully described below will permit the patient to report a color change from yellow to green when the strips are brought into intersecting relationship in the visual axis of the respective left or right eye of the patient being measured.

It will be understood by those skilled in the art that any combination of complimentary colors or other color change arrangement can be used for the respective horizontal and vertically adjustable strips without departing from the scope of the present invention.

In order to adjustably index or position the vertical strips 20a and 20b and the horizontal strips 21a and 21b relative to each other and relative to the respective eye viewing openings 13a and 13b, these strips are connected as by hubs 22a and 22b on the vertical strips 20a and 20b and hubs 23a and 23b on the horizontal strips 21a and 21b respectively to threaded members 24a, 24b, 25a, and 25b. The threaded members in turn are journalled in their respective spaced journal bearings on the main frame 10 as at 26a and 26'a for threaded member 24a ; 26b and 26'b for threaded member 24b; 27a and 27'a for threaded members 25a, and 27b and 27'b for threaded member 25b as is shown in FIGS. 1 to 5 of the drawings.

FIGS. 1 to 5 of the drawings further show that each of the threaded members 24a, 24b, 25a and 25b are provided with handles respectively at 29a for threaded member 24a, 29b for threaded member 24b, 30a for threaded member 25a, and 30b for threaded member 25b. When these threaded members are turned clockwise the vertical and horizontal strips move in one direction and when the handles are turned counterclockwise, the vertical and horizontal strips move respectively in the other direction.

As is clear from FIGS. 1, 3, 4 and 5 the respective horizontal strips 21a and 21b lie in a plane which is in front of the respective vertical strips 20a and 20b and the vertical strips in turn lie in and move in a vertical plane which is in front of the eye viewing openings 13a and 13b. Therefore the respective vertical and horizontal strips can be moved in intersecting relationship relative to each other and at the same time can be moved relative to the eye viewing openings 13a and 13b.

Further the position of the horizontally disposed strips 20a and 20b allows for spring clips as at 31a and 31'a and 31b and 31'b to be provided thereon for snapping or mounting a corrective lens as shown at 31c on the clips 31b and 31'b of horizontally disposed strip 21b in FIG. 1 of the drawings.

Index markings or graduations 32 are provided on the transverse member 11 and are disposed to extend thereon from the center zero point 33 in opposite directions on either side thereof in the conventional centimeter and millimeter graduations.

The zero centerpoint is necessary to enable the instrument frame to be placed in alignment with the center point of the eyeglass frame selected by the patient on which the ophthalmic measuring instrument 10 will be mounted in order to make the subjective measurement and thus to position the vertically disposed members 20a and 20b in the visual axis of the respective right eye and left eye of the patient. In order to facilitate an accurate reading of this distance the pointers as at 34a and 34b will be provided on each of the respective vertically disposed transparent strips 20a and 20b.

Similarly each of the respective side sections 12a and 12b are provided with graduated markings as at 35a and 35b, the zero point therefor being shown at 36a and 36b. The graduated markings are operatively associated with the pointers 37a as at FIG. 5 and 37b on the respective hubs 23a and 23b of the horizontally disposed transverse members 21a and 21b.

Figure 3:
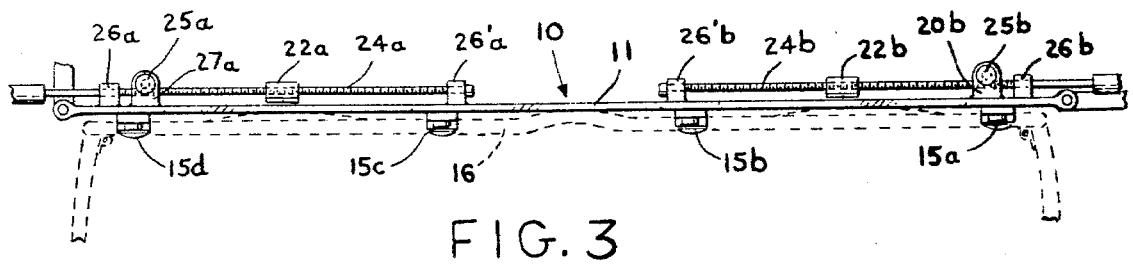
FIG. 3 is a top plane view of an ophthalmic measuring instrument as applied to the selected eyeglass frame as shown in FIG. 2.
Figure 4:
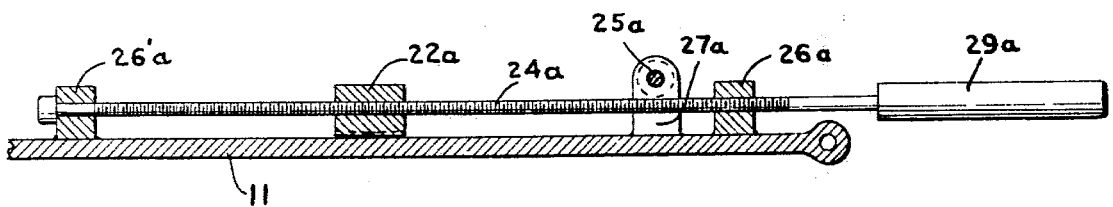
FIG. 4 is a horizontal section taken on line 4—4 of FIG. 1.
Figure 5:
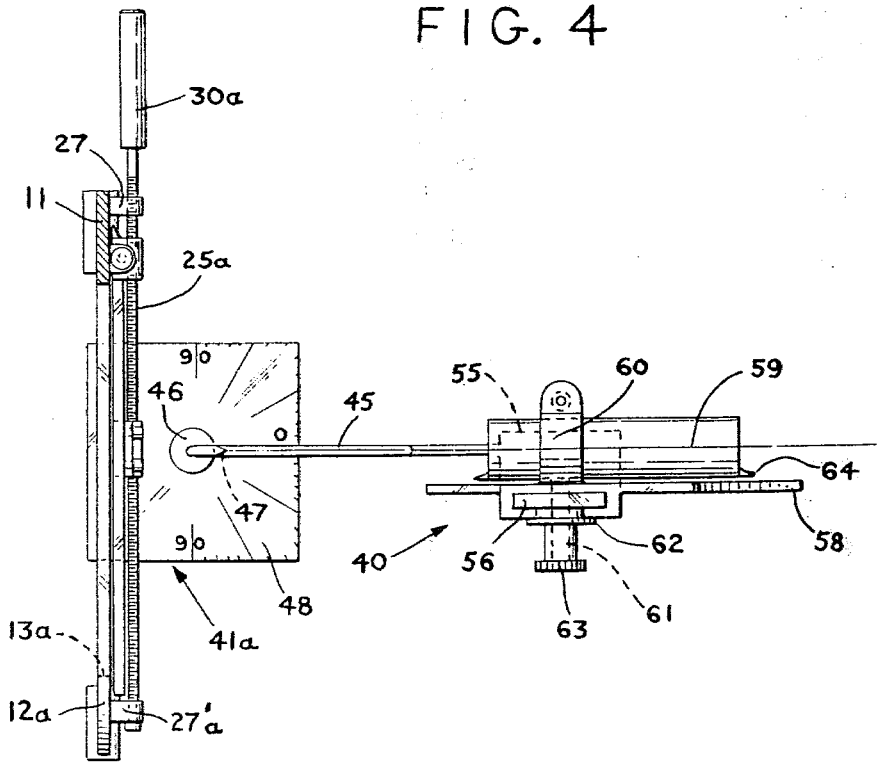
FIG. 5 is a vertical section taken on line 5—5 of FIG. 1.

In utilizing the ophthalmic measuring instrument to measure the exact position of the patient's visual axes, the center of the bridge on the eyeglass frame selected by the patient is marked by halfing the measured distance across the eyeglass wire of the eyeglass frame. The zero centerpoint 33 on the instrument frame 10 is aligned with this marked point and the instrument frame 10 is clipped to the patient's eyeglass frames 16 as is shown in FIGS. 2 and 3 of the drawings and the assembled eyeglass frame and ophthalmic measuring instrument are squared with each other and placed squarely in position on the bridge of the patient's nose. The patient is then given a colored card with a specifically sized white square target thereon and is requested to hold the same at a measured working distance.

The ophthalmic measuring instrument in accordance with the present invention will be used with colored cards having different sized white target squares thereon. The size of the squares on the card will vary according to the working distance and the visual angle subtended through the sized horizontal and vertical strips. For example, for a distance of 10" from the instrument frame the white target will be 13 mm. ×13 mm.; for a distance of 16" the white target will be 15 mm. ×15 mm., and for 20" the target will be 20 mm. ×20 mm. The reason for such specifically sized targets is to equal in width that angle subtended by the narrow sized fitter strips 20b and 21b at the measured working distance.

Now the examiner adjusts the vertically disposed strips 20a and 20b until the patient advises that the white target color has changed to yellow. Then, the examiner adjusts the horizontally disposed strips 21a and 21b until the patient advises that the color of the target has changed to green.

The MVA distance for the respective left eye and right eye are now read from the zero counterpoint 33 on the upper index markings or graduations 32. The vertical position for the respective eyes can be read on the side index markings or graduations as at 35a and 35b for the vertical displacement of the respective right and left eyes of the patient will be the difference between these readings.

There is thus provided a device which standardizes and eliminates the potential for error by the subjective determination of the near point and far point MVA measurements and for the vertical displacement of a patient's eyes.

ANGLE MEASURING ATTACHMENT

Additionally, the ophthalmic measuring instrument in accordance with the present invention provides angle measuring attachment generally designated 40 for measuring the vertical inclination of the visual axis as well as the vergence angles of the respective eyes in near viewing, which measurements are also critical to the prescription of lenses, telescopes and/or microscopes for patients with special optical needs.

This attachment is more fully described and claimed in the said co-pending parent application Ser. No. 809,536 from which the present application was divided and accordingly will not be more fully described herein.

Thus, the improved ophthalmic measuring instrument in accordance with the present invention will provide an improved measuring device and method which has the following advantages.

1. It utilizes subjective measurement of the visual axis of the eye rather than measurement of the pupillary axis.
2. It establishes a new standard procedure and eliminates error for prescribing and designing lenses.
3. It allows a monocular measurement rather than a binocular measurement.
4. It takes both horizontal and vertical measurements to allow for facial and/or optical asymmetries.

It will be understood that the invention is not to be limited to the specific construction or arrangement of parts shown but that they may be widely modified within the invention defined by the claims.

What is claimed is:

1. An ophthalmic measuring instrument to be detachably connected to the eyeglass frame of a patient in front of the lens area in said eyeglass frame comprising,
   a. an instrument frame having a front, a back, spaced eye viewing openings and a medially disposed nose opening,
   b. clip means on the back of said frame for detachably connecting the instrument frame to the eyeglass frame of the patient so that the eye viewing openings are disposed substantially in front of and in alignment with the lens area of said eyeglass frame,
   c. first and second vertically disposed transparent colored strips adjustably connected to the instrument frame to permit indexing of each of said strips in front of an associated one of said eye viewing openings,
   d. said first and second vertically disposed transparent colored strips respectively having a width not greater than $3\frac{1}{2}$ mm.,
   e. first and second horizontally disposed transparent colored strips adjustably connected to the instrument frame to permit indexing of each of said strips in front of an associated one of said eye viewing windows in intersecting relation with an associated one of said vertically disposed colored strips,
   f. said first and second horizontally disposed transparent colored strips respectively having a width not greater than $3\frac{1}{2}$ mm.,
   g. the respective first and second horizontally disposed transparent colored strips having a color which causes a perceptive color change to the patient when the associated transparent colored strips bisect the visual axis of the patient's eye being measured,
   h. graduated upper markings on the front of said frame having a center point to enable the said frame to be aligned with the center of the eyeglass frame to which it is attached and operatively associated with the first and second vertically disposed transparent colored strips to enable an MVA distance measurement to be made whenever either of said vertically disposed transparent colored strips bisect the visual axis of a given eye of the patient,
   i. a first and second set of graduated markings on the front of said frame operatively associated with the first and second horizontally disposed transparent colored strips to permit the vertical displacement between the patient's respective eyes to be measured when the horizontally disposed transparent colored strips are in the visual axis of the patient.

2. In an ophthalmic measuring instrument as claimed in claim 1 wherein the color of the respective horizontal transparent colored strips are complimentary to the color of the associated vertical transparent colored strips, and said horizontal and vertical colored strips are in a range from 2 to $3\frac{1}{2}$ mm.

3. In an ophthalmic measuring instrument as claimed in claim 1 wherein, each of said first and second horizontally disposed transparent colored strips are provided with means for holding a corrective lens therein when the horizontal strip is in position in the visual axis of the patient.

* * * * *